「12) United States Patent
Bouchard et al.

(10) Patent No.: US 7,816,543 B2
(45) Date of Patent: Oct. 19, 2010

(54) LEPTOMYCIN DERIVATIVES

(75) Inventors: Herve Bouchard, Thiais (FR); Alain Commercon, Vitry-sur-Seine (FR); Ravi V. J. Chari, Newton, MA (US)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 12/276,568

(22) Filed: Nov. 24, 2008

(65) Prior Publication Data

US 2009/0182038 A1 Jul. 16, 2009

Related U.S. Application Data

(63) Continuation of application No. PCT/IB2007/001328, filed on May 23, 2007.

(30) Foreign Application Priority Data

Jun. 9, 2006 (EP) .................................. 06290948

(51) Int. Cl.
*C07D 309/30* (2006.01)
(52) U.S. Cl. ...................................................... 549/293
(58) Field of Classification Search .................. 549/293
See application file for complete search history.

(56) References Cited

U.S. PATENT DOCUMENTS

| 4,771,070 | A | 9/1988 | Hokanson et al. |
| 4,792,522 | A | 12/1988 | Nettleton et al. |
| 7,446,196 | B2 * | 11/2008 | Dong et al. .................. 544/149 |
| 2003/0162740 | A1 | 8/2003 | Wang et al. |
| 2005/0287155 | A1 | 12/2005 | Santi et al. |

FOREIGN PATENT DOCUMENTS

| WO | WO 01/07013 | 2/2001 |
| WO | WO 02/062396 | 8/2002 |
| WO | WO 2005/117894 | 12/2005 |
| WO | WO 2005/117986 | 12/2005 |

OTHER PUBLICATIONS

Dorwald F. A. Side Reactions in Organic Synthesis, 2005, Wiley: VCH, Weinheim p. IX of Preface p. 1-15.*
Blattler, W. A., et. al., Drugs to Enhance the Therapeutic Potency of Anticancer Antibodies: Antibody-Drug Conjugates as Tumor-Activated Prodrugs, Anticancer Agents, Frontiers in Cancer Chemotherapy, pp. 317-338, ACS Symposium Series 796, (2001), Chapter 19.
Bumol, T. F., et. al., KS1/4-Davlb, A Monoclonal Antibody-Vinca Alkaloid Conjugate for Site-Directed Therapy of Epithelial Malignancies, Antibody Mediated Delivery Systems, pp. 55-79, (1988).
Chari, R. V. J., et. al., Immunoconjugates Containing Novel Maytansinoids: Promising Anticancer Drugs, Cancer Research, vol. 52, pp. 127-131, (1992).
Chari, R. V. J., et. al., Targeted Delivery of Chemotherapeutics Tumor-Activated Prodrug Therapy, Advanced Drug Delivery Reviews, vol. 31, (1998), pp. 89-104.

Diener, E., et. al., Experimental Application of Target-Specific Immunoconjugates Containing Daunomycin as the Cytocidal Component, Antibody Mediated Delivery Systems, pp. 1-23, (1988).
Dillman, R. O., et. al., Preclinical Trials with Combinations and Conjugates of T101 Monoclonal Antibody and Doxorubicin1, Cancer Research, vol. 46, pp. 4886-4891, (1986).
Endo, N., et, al., In Vitro Cytotoxicity of a Human Serum Albumin-Mediated Conjugate of Methotrexate with Anti-MM46 Monoclonal Antibody, Cancer Research, vol. 47, pp. 1076-1080, (1987).
Garnett, M. C., et. al., An Improved Synthesis of a Methotrexate-Albumin-791T/36 Monoclonal Antibody Conjugate Cytotoxic to Human Osteogenic Sarcoma Cell Lines, Cancer Research, vol. 46, pp. 2407-2412, (1986).
Ghetie, M-A., et. al., Evaluation of Ricin A Chain-Containing Immunotoxins Directed Against CD19 and CD22 Antigens on Normal and Malignant Human B-Cells as Potential Reagents for In Vivo Therapy, Cancer Research, vol. 48, pp. 2610-2617, (1988).
Ghose, T., et. al., Antibody-Directed Drug Targeting in Cancer Therapy, Targeted Drugs, pp. 1-22, (1983), Chapter 1.
Hamamoto, T., et. al., Leptomycins A and B, New Antifungal Antibiotics I. Taxonomy of the Producing Strain and Their Fermentation, Purification and Characterization, The Journal of Antibiotics, vol. 36, No. 6, pp. 639-645, (1983).
Hamann, P. R., et. al., An Anti-CD33 Antibody-Calicheamicin Conjugate for Treatment of Acute Myeloid Leukemia. Choice of Linker, Bioconjugate Chem., (2002), vol. 13, pp. 40-46.
Hinman, L. M., et. al., Preparation and Characterization of Monoclonal Antibody Conjugates of the Calicheamicins: A Novel and Potent Family of Antitumor Antibiotics, Cancer Research, vol. 53, pp. 3336-3342, (1993).
Huang, S-Y., et. al., A Polyethylene Glycol Copolymer for Carrying and Releasing Multiple Copies of Cysteine-Containing Peptides, Bioconjugate Chemistry, (1998), vol. 9, pp. 612-617.
Hurwitz, E., et. al., Soluble Macromolecules as Carriers for Daunorubicin, Journal of Applied Biochemistry, vol. 2, pp. 25-35, (1980).
Kalesse, M., et. al.,, The Chemistry and Biology of the Leptomycin Family, Synthesis, (2002), vol. 8, pp. 981-1003.
Kato, Y., et. al., A Novel Method of Conjugation of Daunomycin with Antibody with a Poly-L-Glutamic Acid Derivative as Intermediate Drug Carrier. An Anti-a-Fetoprotein Antibody-Daunomycin Conjugate, J. Med. Chem., (1984) vol. 27, pp. 1602-1607.
Komiyama, K., et. al., Antitumor Activity of Leptomycin B, The Journal of Antibiotics, vol. 38, No. 3, pp. 427-429, (1985).
Lambert, J. M., et. al., Immunotoxins Containing Single Chain Ribosome-Inactivating Proteins, Immunotoxins, (1988), pp. 175-209.

(Continued)

*Primary Examiner*—D. Margaret Seaman
*Assistant Examiner*—Nizal S Chandrakumar
(74) *Attorney, Agent, or Firm*—Jiang Lin

(57) ABSTRACT

Leptomycin derivatives having a moiety, such as a sulfide or a disulfide, that can conjugate to a cell binding reagent such as an antibody are disclosed. The therapeutic use of such leptomycin derivative conjugates is also described; such conjugates have therapeutic use because they can deliver cytotoxic leptomycin derivatives to a specific cell population in a targeted fashion.

17 Claims, 1 Drawing Sheet

OTHER PUBLICATIONS

Lambert, J. M., et. al., Purified Immunotoxins That Are Reactive With Human Lymphoid Cells, The Journal of Biological Chemistry, vol. 260, No. 22, (1985), pp. 12035-12041.

Liu, C., et. al., Eradication of Large Colon Tumor Xenografts By Targeted Delivery of Maytansinoids, Proc. Natl. Acad. Sci. USA, vol. 93, pp. 8618-8623, (1996).

Manabe, Y., et. al., Production of a Monoclonal Antibody-Mitomycin C Conjugate, Utilizing Dextran T-40, and Its Biological Activity, Biochemical Pharmacology, vol. 34, No. 2, pp. 289-291, (1985).

Ohkawa, K., et. al., Evaluation of a Conjugate of Purified Antibodies Against Human AFP-Dextran-Daunorubicin to Human AFP-Producing Yolk Sac Tumor Cell Lines, Cancer Immuno Immunother, (1986), vol. 22, pp. 81-86.

Ojima, I., et. al., Rhodium-Catalyzed Carbonylative Silycarbocyclization (Co-Sicac) of 1,6-Enynes, American Chemical Society, pp. 1, (2001), vol. 78.

Pietersz, G. A., et. al., Antibody-Targeted Drugs for the Therapy of Cancer, Journal of Drug Targeting, (1994), vol. 2, pp. 183-215.

Pietersz, G. A., et. al., The Linkage of Cytotoxic Drugs to Monoclonal Antibodies for the Treatment of Cancer, Bioconjugate Chemistry, (1990), vol. 1, No. 2, pp. 89-95.

Pietersz, G. A., et. al., The use of Anthracycline-Antibody Complexes for Specific Antitumor Activity, Antibody Mediated Delivery Systems, pp. 25-53, (1988).

Sela, M., et. al., Conjugates of Antibodies with Cytotoxic Drugs, Immunoconjugates, pp. 189-216, (1987).

Shouval, D., et. al., Doxorubicin Conjugates of Monoclonal Antibodies to Hepatoma-Associated Antigens, Proc. Natl. Acad. Sci., vol. 85, pp. 8276-8280, (1988).

Tsukada, Y., et. al., An Anti-a-Fetoprotein Antibody-Daunorubicin Conjugate With a Novel Poly-L-Glutamic Acid Derivative as Intermediate Drug Carrier, J. Natl. Canc. Inst., vol. 73, No. 3, (1984), pp. 721-729.

Tsukada, Y., et. al., Suppression of Human a-Foetoprotein-Producing Hepatocellular Carcinoma Growth in Nude Mice by an Anti a-Foetoprotein Antibody-Daunorubicin Conjugate with a Poly-L-Glutamic Acid Derivatives as Intermediate Drug Carrier, Br. J. Cancer, (1985), vol. 52, pp. 111-116.

Ojima, I., et. al., Computational Analysis of the Paclitaxel Binding Site in a-Tubulin, American Chemical Society pp. 1, (2001), vol. 78.

Ojima, I, et. al., Design, Synthesis and Sar Studies of 3' N Modified Second Generation Taxoids, American Chemical Society, pp. 1, (2001), vol. 78.

Ojima, I., et. al., Synthesis of Labeled Ligands for Solid State Nmr Studies of the Taxoids-Microtubule Interaction, American Chemical Society, pp. 1, (2001), vol. 78.

Ojima, I., et. al., Efficient Route to Triols and Polyols Via Rhodium-Catalyzed Intramolecular Silyformylation of Alkynes, American Chemical Society, pp. 1, (2001), vol. 78.

* cited by examiner

LEPTOMYCIN DERIVATIVES

FIELD OF THE INVENTION

The present invention relates to novel leptomycin derivatives and their therapeutic uses. More specifically, the invention relates to novel leptomycin derivatives which contain a moiety (linking group) that can be covalently bond to a cell binding agent, and the corresponding conjugates comprising said leptomycin derivative bond via a linker to said cell binding agent. Said conjugates provide therapeutic agents capable of being activated and released in vivo, and delivered to specific cell populations in a targeted manner.

BACKGROUND OF THE INVENTION

Many reports have appeared which are directed to the targeting of tumor cells with monoclonal antibody-drug conjugates {Sela et al, in Immunoconjugates, pp. 189-216 (C. Vogel, ed. 1987); Ghose et al, in Targeted Drugs, pp. 1-22 (E. Goldberg, ed. 1983); Diener et al, in Antibody Mediated Delivery Systems, pp. 1-23 (J. Rodwell, ed. 1988); Pietersz et al, in Antibody Mediated Delivery Systems, pp. 25-53 (J. Rodwell, ed. 1988); Bumol et al, in Antibody Mediated Delivery Systems, pp. 55-79 (J. Rodwell, ed. 1988); G. A. Pietersz & K. Krauer, 2 J. Drug Targeting, 183-215 (1994); R. V. J. Chari, 31 Adv. Drug Delivery Revs., 89-104 (1998); W. A. Blattler & R. V. J. Chari, in Anticancer Agents, Frontiers in Cancer Chemotherapy, 317-338, ACS Symposium Series 796; and 1. Ojima et al eds, American Chemical Society 2001}. Cytotoxic drugs such as methotrexate, daunorubicin, doxorubicin, vincristine, vinblastine, melphalan, mitomycin C, chlorambucil, calicheamicin and maytansinoids have been conjugated to a variety of murine monoclonal antibodies. In some cases, the drug molecules were linked to the antibody molecules through an intermediary carrier molecule such as serum albumin {Garnett et al, 46 Cancer Res. 2407-2412 (1986); Ohkawa et al, 23 Cancer Immunol. Immunother. 81-86 (1986); Endo et al, 47 Cancer Res. 1076-1080 (1980)}, dextran {Hurwitz et al, 2 Appl. Biochem. 25-35 (1980); Manabi et al, 34 Biochem. Pharmacol. 289-291 (1985); Dillman et al, 46 Cancer Res. 4886-4891 (1986); and Shoval et al, 85 Proc. Natl. Acad. Sci. U.S.A. 8276-8280 (1988)}, or polyglutamic acid {Tsukada et al, 73 J. Natl. Canc. Inst. 721-729 (1984); Kato et al, 27 J. Med. Chem. 1602-1607 (1984); Tsukada et al, 52 Br. J. Cancer 111-116 (1985)}.

A wide array of linkers is now available for the preparation of such immunoconjugates, including both cleavable and non-cleavable linkers. In vitro cytotoxicity tests, however, have revealed that antibody-drug conjugates rarely achieve the same cytotoxic potency as the free unconjugated drugs. This has suggested that mechanisms by which drug molecules are released from conjugated antibodies are very inefficient. Early work in the area of immunotoxins showed that conjugates formed via disulfide bridges between monoclonal antibodies and catalytically active protein toxins were more cytotoxic than conjugates containing other linkers {Lambert et al, 260 J. Biol. Chem. 12035-12041 (1985); Lambert et al, in Immunotoxins 175-209 (A. Frankel, ed. 1988); Ghetie et al, 48 Cancer Res. 2610-2617 (1988)}. This improved cytotoxicity was attributed to the high intracellular concentration of reduced glutathione contributing to the efficient cleavage of the disulfide bond between the antibody molecule and the toxin. Maytansinoids and calicheamicin were the first examples of highly cytotoxic drugs that had been linked to monoclonal antibodies via disulfide bonds. Antibody conjugates of these drugs have been shown to possess high potency in vitro and exceptional antitumor activity in human tumor xenograft models in mice {R. V. J. Chari et al., 52 Cancer Res., 127-131 (1992); C. Liu et al., 93, Proc. Natl. Acad. Sci., 8618-8623 (1996); L. M. Hinman et al., 53, Cancer Res., 3536-3542 (1993); and P. R. Hamann et al, 13, BioConjugate Chem., 40-46 (2002)}.

Leptomycin B:

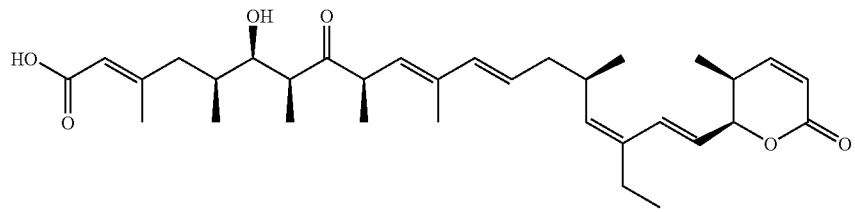

is a natural product originally isolated from *Steptomyces* spp., as reported in U.S. Pat. No. 4,771,070 and U.S. Pat. No. 4,792,522. It was originally identified as a result for screening for anti-microbial activity and subsequently identified as an anti-tumour agent (Komiyama et al., J. Antibiotics 1985, 38(3), 427-429 and US 2003/0162740). At the molecular level, leptomycin B acts as an inhibitor of the nuclear export receptor CRM1, which binds to and affects the nuclear translocation of "cargo proteins". At the cellular level, leptomycin B acts by arresting cells at the end of the G1 and G2 phases of the cell cycle (Kalesse et al., Synthesis 2002, 8, 981-1003). However, its extreme toxicity towards mammalian cells (Hamamoto et al., J. Antibiotics 1983, 36(6), 639-645) made its clinical use impossible. It is thus highly desirable to reduce toxicity of leptomycin derivatives towards non-targeted cells.

The therapeutic efficacy of leptomycin derivatives could be greatly improved by changing the in vivo distribution through targeted delivery to the tumor site, resulting in lower toxicity to non-targeted tissues, and thus, lower systemic toxicity. In order to achieve this goal, the present inventors have considered preparing conjugates of derivatives of leptomycin B with cell-binding agents that specifically target tumor cells, with a view to display high target-specific cytotoxicity.

SUMMARY OF THE INVENTION

The object of the present invention is to provide leptomycin derivatives which contain a linking group that can be covalently bond to a cell binding agent, and the corresponding conjugates comprising said leptomycin derivative bond via a linker to said cell binding agent. Said conjugates provide therapeutic agents capable of being activated and released in vivo, and delivered to specific cell populations in a targeted manner. In order to further enhance water solubility, an optional polyethylene glycol spacer can be introduced into the linking group.

The compounds of the invention can be used in cytotoxic conjugates in which a cell binding agent is linked to one or more of the compounds of the present invention. Cell binding agents include antibodies and fragments thereof, interferons, lymphokines, vitamins, hormones and growth factors. Pharmaceutical compositions containing such conjugates are also provided.

The cytotoxic conjugates can be used in a method for treating a subject by administering an effective amount of the above pharmaceutical composition. According to the cell-type to which the selected cell binding agent binds, many diseases may be treated either in vivo, ex vivo or in vitro. Such diseases include, for example, the treatment of many kinds of cancers, including lymphomas, leukemias, cancer of the lung, breast, colon, prostate, kidney, pancreas, and the like.

Thus, there are provided leptomycin derivatives which are useful in the targeting of specific cell types by means of conjugation to a specific cell binding agent.

DETAILED DESCRIPTION OF THE INVENTION

Figure 1:
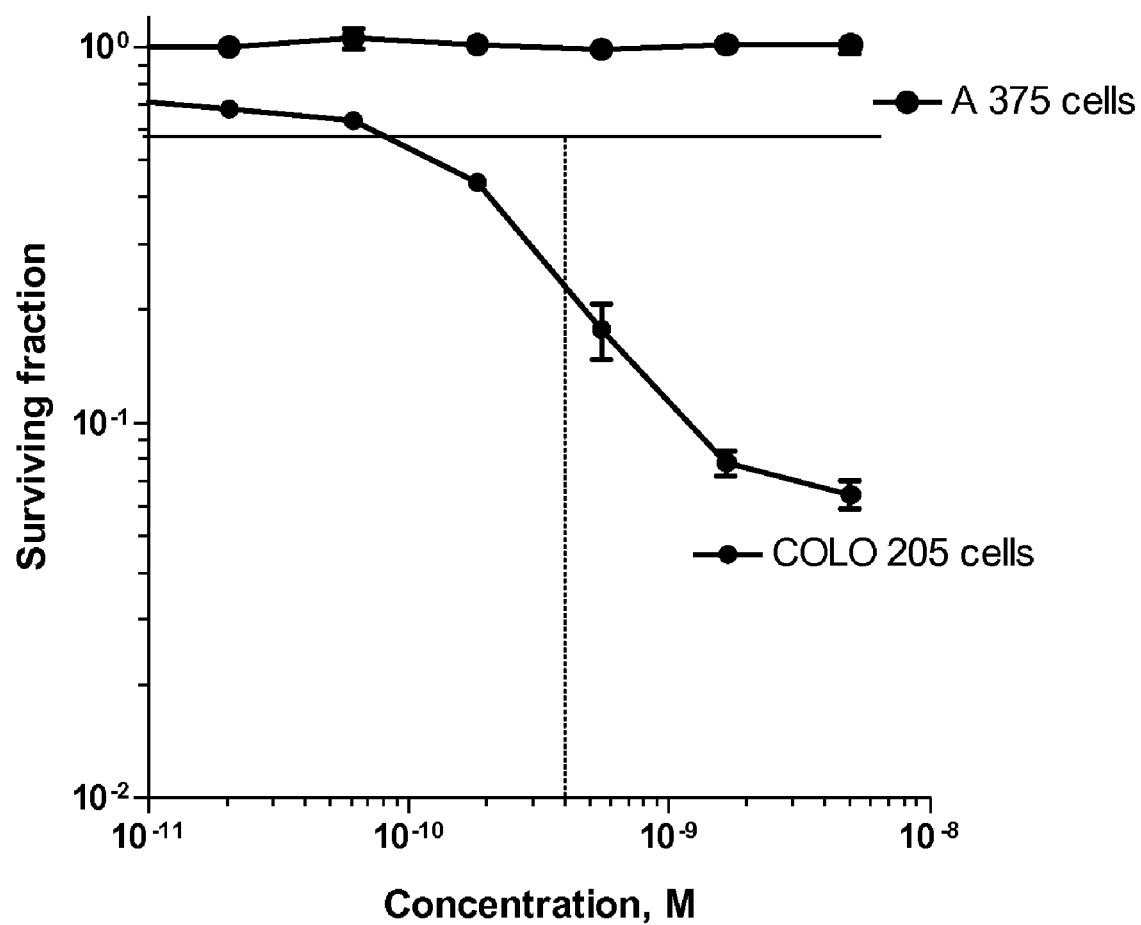
FIG. 1 shows the in vitro cytotoxicity and specificity of the conjugate huC242-SSNPB-Leptomycin derivative of example 6.

The present inventors have found leptomycin derivatives which are capable of linkage to cell binding agents whereby the therapeutic efficacy of such derivatives is improved by changing the in vivo distribution through targeted delivery of the derivatives to the tumor site, resulting in a lower toxicity to non-targeted tissues, and hence lower systemic toxicity.

In order to achieve this goal, the inventors synthesized exemplary leptomycin derivatives which comprise a linking group for conjugation of the leptomycin derivative to a cell binding agent. The linking group can contain a polyethylene glycol spacer. The linking group is used for conjugation to cell binding agents, and preferably comprises a disulfide bond or a sulfide (or called herein thioether) bond.

It has previously been shown that the linkage of highly cytotoxic drugs to antibodies using a cleavable link, such as a disulfide bond, ensures the release of fully active drug inside the cell, and that such conjugates are cytotoxic in an antigen specific manner {R. V. J. Chari et al, 52 Cancer Res. 127-131 (1992); R. V. J. Chari et al., 55 Cancer Res. 4079-4084 (1995); and U.S. Pat. Nos. 5,208,020 and 5,475,092}. In the present invention, the inventors describe the synthesis of leptomycin derivatives, procedures for their conjugation to monoclonal antibodies and for measurement of the in vitro cytotoxicity and specificity of such conjugates. Thus the invention provides useful compounds for the preparation of therapeutic agents directed to the elimination of diseased or abnormal cells that are to be killed or lysed such as tumor cells, virus infected cells, microorganism infected cells, parasite infected cells, autoimmune cells (cells that produce auto-antibodies), activated cells (those involved in graft rejection or graft vs. host disease), or any other type of diseased or abnormal cells, while exhibiting minimal side effects.

Thus, this invention teaches the synthesis of leptomycin derivatives that can be chemically linked to a cell binding agent and that maintain, upon release of the protective group, the high cytotoxicity of the parent leptomycin derivatives. These compounds when linked to a cell binding agent are cytotoxic to cells to which the cell binding agent binds and are much less toxic to non-target cells.

Leptomycin Derivatives of the Invention

The leptomycin derivatives according to the present invention comprise a linking group capable of conjugating the derivative to a cell binding agent.

According to the present invention, "leptomycin derivatives" refer to members of the leptomycin family as defined in Kalesse et al in Synthesis 2002, 8, 981-1003, and includes: leptomycins, such as leptomycin A and leptomycin B, callystatins, ratjadones such as ratjadone A and ratjadone B, anguinomycins such as anguinomycin A, B, C, D, kasusamycins, leptolstatin, leptofuranins, such as leptofuranin A, B, C, D. Derivatives of leptomycin A and B are preferred.

In order to link the derivative to a cell-binding agent, the derivative must include a moiety (linking group) that allows the derivatives to be linked to a cell binding agent via a linkage such as a disulfide bond, a sulfide (or called herein thioether) bond, an acid-labile group, a photo-labile group, a peptidase-labile group, or an esterase-labile group. The derivatives are prepared so that they contain a moiety necessary to link the leptomycin derivative to a cell binding agent via, for example, a disulfide bond, a thioether bond, an acid-labile group, a photo-labile group, a peptidase-labile group, or an esterase-labile group. In order to further enhance solubility in aqueous solutions, the linking group can contain a polyethylene glycol spacer.

Preferably, a sulfide or disulfide linkage is used because the reducing environment of the targeted cell results in cleavage of the sulfide or disulfide and release of the derivatives with an associated increase in cytotoxicity.

According to a preferred aspect, the present invention provides leptomycin derivatives wherein the terminal carbonyl function represents a moiety that enables linkage of the derivative to a cell binding agent. The linking moiety may contain a polyethylene glycol spacer. Examples include moieties that enable linkages via disulfide bond, a thioether bond, an acid-labile group, a photo-labile group, a peptidase-labile group, or an esterase-labile group, and are well-known in the art {see, e.g., U.S. Pat. No. 5,846,545, which is incorporated herein by reference}. Preferred moieties are those that enable linkage via a disulfide bond, for example a thiol or a disulfide. Mixed disulfides containing any terminal leaving group, such as glutathione, alkyl thio such as methylthio, pyridylthio, arylthio, nitropyridylthio, hydroxycarbonylpyridylthio, (nitro)hydroxycarbonylpyridylthio, and the like may be used provided that such disulfides are capable of undergoing a disulfide-exchange reaction for the coupling of the derivative to a cell binding agent.

More specifically, the derivatives of the invention are of formula (I):

(I)

T—S—(Z)$_n$—Y—X—...—$R_9$—...—$R_a$, $R'_a$—...—$R_{17}$ wherein
Ra and R'a are H or -Alk; preferably Ra is -Alk, preferably methyl and R'a is H;
R17 is alkyl optionally substituted by OR, CN, NRR', perfluoroalkyl; preferably, R17 is alkyl, more preferably methyl or ethyl;
R9 is alkyl optionally substituted by OR, CN, NRR', perfluoroalkyl; preferably, R9 is alkyl, more preferably methyl;
X is —O— or —NR—; preferably, X is —NR—;
Y is —U—, —NR—U—, —O—U—, —NR—CO—U—, —U—NR—CO—, —U—CO—, —CO—U—;
preferably, when X is —O—, Y is —U—, —NR—U—, —U—NR—CO—;
where U is chosen from linear or branched -Alk-, -Alk(OCH$_2$CH$_2$)$_m$—, —(OCH$_2$CH$_2$)$_m$-Alk-, -Alk(OCH$_2$CH$_2$)$_m$-Alk-, —(OCH$_2$CH$_2$)$_m$—, -Cycloalkyl-, -Heterocyclic-, -Cycloalkyl-Alk-, -Alk-Cycloalkyl-, -Heterocyclic-Alk-, -Alk-Heterocyclic-;
Where m is an integer chosen from 1 to 2000;
Preferably, U is linear or branched -Alk-,
Z is -Alk-;
n is 0 or 1; preferably n is 0;
T represents H, a thiol protecting group such as Ac, R$_1$ or SR$_1$, wherein R$_1$ represents H, methyl, Alk, Cycloalkyl, optionally substituted aryl or heterocyclic, or T represents 3S)-3-methyl-6-oxo-3,6-dihydro-2H-pyran-2-yl)-8-oxo-nonadeca-2,10,12,16,18-pentaenoic acid (2-Methyl-2-methyldisulfanyl-propyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid (2-Mercapto-2-methyl-propyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid or their pharmaceutically acceptable salts, hydrates, or hydrated salts, or the polymorphic crystalline structures of these compounds or their optical isomers, racemates, diastereomers or enantiomers.

As defined herein, alkyl includes linear or branched $C_1$-$C_{20}$ alkyls. Examples of linear alkyls include methyl, ethyl, propyl, butyl, pentyl and hexyl. Examples of branched alkyls include isopropyl, isobutyl, sec.-butyl, tert-butyl, isopentyl and 1-ethyl-propyl. Examples of cycloalkyls, i.e. cyclic alkyls, include cyclopropyl, cyclobutyl, cyclopentyl and cyclohexyl. Examples of aryls include phenyl and naphthyl. Examples of substituted aryls include aryls such as phenyl or naphthyl substituted with alkyl groups, with halogens, such as Cl, Br, F, nitro groups, amino groups, sulfonic acid groups,

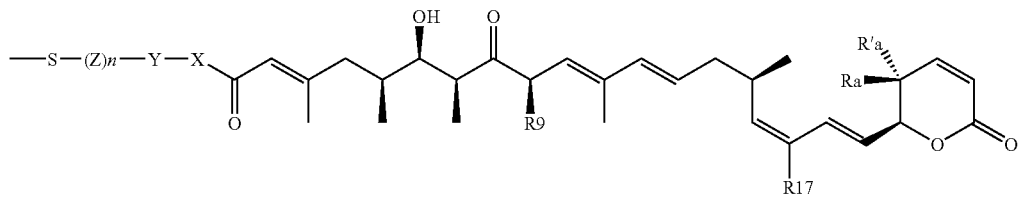

where:
Ra, R'a, R17, R9, X, Y, Z, n are defined as above;
preferably, T is H or SR$_1$, wherein R$_1$ represents Alk, more preferably methyl;
R, R' identical or different are H or alkyl;
Alk represents a linear or branched alkyl; preferably Alk represents (—(CH$_{2-q}$(CH$_3$)$_q$)$_p$— where p represents an integer from 1 to 10; and q represents an integer from 0 to 2; preferably, Alk represents —(CH$_2$)— or —C(CH$_3$)$_2$—.

or their pharmaceutically acceptable salts, hydrates, or hydrated salts, or the polymorphic crystalline structures of these compounds or their optical isomers, racemates, diastereomers or enantiomers.

Preferred compounds may be chosen from:
(2-Methylsulfanyl-ethyl)-amide of (2E,10E,12E,16Z,18E)-(R)-6-Hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid Bis-[(2-mercaptoethyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid]

(2-Mercapto-ethyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid (2-Methyldisulfanyl-ethyl)-amide of (2E,10E,12E,16Z,18E)-(R)-6-hydroxy-3,5,7,9,11,15,17-heptamethyl-19-((2S, carboxylic acid groups, hydroxy groups and alkoxy groups. Heterocyclics refer to optionally aromatic rings, comprising one or more heteroatoms selected from O, N, and S, and examples include furyl, pyrrollyl, pyridyl, (e.g., a 2-substituted pyrimidine group) and thiophene.

Sulfide or disulfide-containing and mercapto-containing derivatives of the present invention can be evaluated for their ability to suppress proliferation of various unwanted cell lines in vitro under incubation conditions. Cell lines such as, for example, Ramos cell line and HL60 can easily be used for the assessment of the cytotoxicity of these compounds. Cells to be evaluated can be exposed to the compounds for 24 hours and the surviving fractions of cells measured in direct assays by known methods. $IC_{50}$ values can then be calculated from the results of the assays.

As used therein, the expression "linkable to a cell binding agent" refers to the leptomycin derivatives comprising at least one linking group, or a precursor thereof, suitable to bond said derivatives to a cell binding agent; preferred linking groups are thiol, sulfide or disulfide bonds, or precursors thereof.

As used therein, the expression "linked to a cell binding agent" refers to the conjugate molecule comprising at least one leptomycin derivative bound to a cell binding agent via a suitable linking group, or a precursor thereof; preferred linking groups are thiol, sulfide or disulfide bonds, or precursors thereof.

As used herein, the term "patient" refers to either an animal, such as a valuable animal for breeding, company or preservation purposes, or preferably a human or a human child, which is afflicted with, or has the potential to be afflicted with one or more diseases and conditions described herein.

As used herein, a "therapeutically effective amount" refers to an amount of a compound of the present invention which is effective in preventing, reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, the terms "pharmaceutically acceptable" refer to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, the disclosure of which is hereby incorporated by reference.

According to a still further object, the present invention is also concerned with the process of preparation of the compounds of the invention.

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, Wiley-VCH Publishers, 1999.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, 3$^{rd}$ ed., John Wiley and Sons, 1999; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary after distilling off the solvent from the reaction mixture, pouring the residue into water followed by extraction with a water-immiscible organic solvent and distilling off the solvent from the extract. Additionally, the product can, if desired, be further purified by various well known techniques, such as recrystallization, reprecipitation or the various chromatography techniques, notably column chromatography or preparative thin layer chromatography.

The process of preparation of the compounds of formula (I) comprises the step of reacting corresponding compounds of formula (II) and (III):

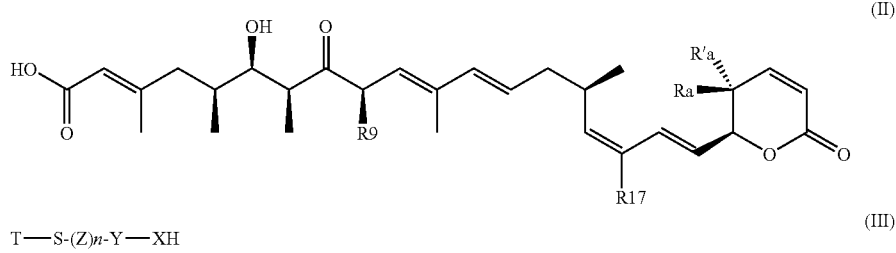

(II)

T—S-(Z)n-Y—XH  (III)

wherein Ra, R'a, R17, R9, X, Y, Z, T, n are defined as in formula (I).

Generally, this reaction may be carried out in the presence of usual coupling reagents, including reagents to suppress racemization such as HOBT, and/or dehydration agents used to activate carboxylic acid towards amide or ester formation, such as DIC, DCC.

Typically, this reaction may be carried out in a suitable organic solvent such as dichloromethane.

Where in formula (I), T is H, the reaction may be alternatively carried out with a N-acylating agent, such as pivaloyl chloride, in the presence of a base, including organic bases, such as triethylamine.

Alternatively, where in formula (I), T is H, the compounds of formula (I) may also be obtained from the corresponding compounds of formula (I) where T is S—R1, in the presence of a reduction agent of disulfide bonds, such as trialkylphosphines and more particularly TCEP. This reaction may be generally conducted in aqueous medium such as mixtures of an organic solvent and water, e.g. THF/water.

The dimer compounds of formula (I) may be prepared by reacting a corresponding compound of formula (II) with a corresponding compound of formula (IV):

HX—Y—(Z)n-S—S—(Z)n-Y—XH        (IV)

in the presence of usual coupling reagents, including reagents to suppress racemization such as HOBT, and/or dehydration agents used to activate carboxylic acid towards amide or ester formation, such as DIC, DCC.

Typically, this reaction may be carried out in a suitable organic solvent such as dichloromethane.

The process may also include the further step of isolating the obtained product.

The present invention also concerns a leptomycin derivative conjugate comprising a cell binding agent linked to one or more leptomycin derivatives according to the invention through a linker comprising said linking group.

Preferably, cell binding agents are antibodies or fragments thereof.

Preferably, the linker comprises a —S— or —S—S— group.

Preparation of Cell Binding Agents

Cell binding agents may be of any kind presently known, or that become known, and include peptides and non-peptides. Generally, these can be antibodies (especially monoclonal antibodies) or a fragment of an antibody that contains at least one binding site, lymphokines, hormones, growth factors, nutrient-transport molecules (such as transferrin), or any other cell binding molecule or substance.

More specific examples of cell binding agents that can be used include:

monoclonal antibodies;

single chain antibodies;

fragments of antibodies such as Fab, Fab', F(ab')$_2$ and F$_v$ {Parham, 131 J. Immunol. 2895-2902 (1983); Spring et al, 113 J. Immunol. 470-478 (1974); Nisonoff et al, 89 Arch. Biochem. Biophys. 230-244 (1960)};

interferons;

peptides;

lymphokines such as IL-2, IL-3, IL-4, IL-6;

hormones such as insulin, TRH (thyrotropin releasing hormones), MSH (melanocyte-stimulating hormone), steroid hormones, such as androgens and estrogens;

growth factors and colony-stimulating factors such as EGF, TGFα, insulin like growth factor (IGF-I, IGF-II) G-CSF, M-CSF and GM-CSF {Burgess, 5 Immunology Today 155-158 (1984)}; vitamins, such as folate and transferrin {O'Keefe et al, 260 J. Biol. Chem. 932-937 (1985)}.

Monoclonal antibody technology permits the production of extremely selective cell binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins.

Selection of the appropriate cell binding agent is a matter of choice that depends upon the particular cell population that is to be targeted, but in general monoclonal antibodies are preferred if an appropriate one is available.

For example, the monoclonal antibody MY9 is a murine IgG$_1$ antibody that binds specifically to the CD33 Antigen {J. D. Griffin et al 8 Leukemia Res., 521 (1984)} and can be used if the target cells express CD33 as in the disease of acute myelogenous leukemia (AML). Similarly, the monoclonal antibody anti-B4 is a murine IgG$_1$, that binds to the CD19 antigen on B cells {Nadler et al, 131 J. Immunol. 244-250 (1983)} and can be used if the target cells are B cells or diseased cells that express this antigen such as in non-Hodgkin's lymphoma or chronic lymphoblastic leukemia.

Additionally, GM-CSF which binds to myeloid cells can be used as a cell binding agent to diseased cells from acute myelogenous leukemia. IL-2, which binds to activated T-cells, can be used for prevention of transplant graft rejection, for therapy and prevention of graft-versus-host disease, and for the treatment of acute T-cell leukemia. MSH, which binds to melanocytes, can be used for the treatment of melanoma.

Preparation of Conjugates

Conjugates of the derivatives and a cell binding agent can be formed using any techniques presently known or later developed. Generally, the process of preparation of conjugates of the invention comprises the step of reacting a leptomycin derivative of the invention with a cell binding agent in the presence of a reagent comprising functions reactive towards the linking group of the derivative and the cell binding agent, so that the derivative and the cell binding agent are linked together via a linker comprising said linking group. Preferably, said linker comprises a sulfide or disulfide bond.

Derivatives can be prepared to contain a free amino group and then linked to an antibody or other cell binding agent via an acid labile linker, or by a photolabile linker. The derivatives can be condensed with a peptide having a suitable sequence and subsequently linked to a cell binding agent to produce a peptidase labile linker. Cytotoxic compounds can be prepared to contain a primary hydroxyl group, which can be succinylated and linked to a cell binding agent to produce a conjugate that can be cleaved by intracellular esterases to liberate free leptomycin derivative. Preferably, the derivatives are synthesized to contain a free or protected thiol group, with or without a PEG-containing spacer, and then one or more sulfide, disulfide or thiol-containing derivatives are each covalently linked to the cell binding agent via a disulfide bond or a thioether bond.

Representative conjugates of the invention are conjugates of leptomycin derivatives with antibodies, antibody fragments, epidermal growth factor (EGF), melanocyte stimulating hormone (MSH), thyroid stimulating hormone (TSH), estrogen, estrogen analogs, androgen, and androgen analogs.

Representative examples of the preparation of various conjugates of leptomycin derivatives and cell binding agents are described below.

Disulfide linkers: Antibody huMy-9-6 is a genetically humanized form of the murine monoclonal antibody My-9-6 directed against the CD33 antigen found on the surface of human myeloid cells, including the majority of cases of acute myeloid leukemia (AML) (E. J. Favaloro, K. F. Bradstock, A. Kabral, P. Grimsley & M. C. Berndt, Disease Markers, 5(4): 215 (1987); M. G. Hoffee, D. Tavares, R. J. Lutz, Robert J., PCT Int. Appl. (2004) WO 2004043344). My-9-6 can be used for the preparation of conjugates. The antibody is modified with N-succinimidyl-3-pyridyldithio propionate as previously described {J. Carlsson, H. Drevin & R. Axen, Biochem. J., 173:723 (1978)} to introduce, on the average, 4 pyridyldithio groups per antibody molecule. The modified antibody is reacted with the thiol-containing leptomycin derivative to produce a disulfide-linked conjugate.

Thioether Linkers: Thiol-containing derivatives of the present invention can be linked to antibodies and other cell binding agents via a thioether link as previously described (U.S. Pat. No. 5,208,020). The antibody or other cell binding agent can be modified with the known or commercially available compound such as N-sulfosuccinimidyl-4-(5-nitro-2-pyridyl-dithio)butanoate (SSNPB), N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC). These crosslinking reagents form non-cleavable linkers derived from maleimido-based moieties.

Crosslinking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA) and N-succinimidyl 3-(bromo-acetamido)propionate (SBAP). These crosslinking reagents form non-cleavable linkers derived from haloacetyl-based moieties. The modified cell binding agent can be reacted with a thiol-containing drug to provide a thioether-linked conjugate.

Acid-Labile Linkers: Amino group-containing leptomycin derivatives of the present invention can be linked to antibodies and other cell binding agents via an acid labile linker as previously described {W. A. Blattler et al, Biochemistry 24, 1517-1524 (1985); U.S. Pat. Nos. 4,542,225, 4,569,789, 4,618,492, 4,764,368}.

Similarly, an hydrazido group-containing leptomycin derivative of the present invention can be linked to the carbohydrate portion of antibodies and other cell binding agents via an acid labile hydrazone linker {for examples of hydrazone linkers see B. C. Laguzza et al, J. Med. Chem., 32, 548-555 (1989); R. S. Greenfield et al, Cancer Res., 50, 6600-6607 (1990)}.

Photo-Labile Linkers: Amine group containing leptomycin derivatives of the present invention may be linked to antibodies and other cell binding agents via a photolabile linker as previously described {P. Senter et al, Photochemistry and Photobiology, 42, 231-237 (1985); U.S. Pat. No. 4,625,014}.

Peptidase-Labile Linkers: Amine group containing leptomycin derivatives of the present invention may also be linked to cell binding agents via peptide spacers. It has been previously shown that short peptide spacers between drugs and macromolecular protein carriers are stable in serum but are readily hydrolyzed by intracellular peptidases {A. Trouet et al, Proc. Natl. Acad. Sci., 79, 626-629 (1982)}. The amino group containing leptomycin derivatives may be condensed with peptides using condensing agents such as 1-ethyl-3-(3-dimethylaminopropyl)carbodiimide-HCl (EDC-HCl) to give a peptide derivative that can be linked to cell binding agents.

Esterase-Labile Linkers: Leptomycin derivatives of the present invention bearing a hydroxy alkyl group may be succinylated with succinic anhydride and then linked to a cell binding agent to produce a conjugate that can be cleaved by intracellular esterases to liberate free drug. {For examples see E. Aboud-Pirak et al., Biochem Pharmacol., 38, 641-648 (1989)}.

Conjugates of antibodies, antibody fragments, protein or peptide hormones, protein or peptide growth factors and other proteins are made in the same way by known methods. For example, peptides and antibodies can be modified with cross linking reagents such as N-succinimidyl 3-(2-pyridyldithio) propionate, N-succinimidyl 4-(2-pyridyldithio)pentanoate (SPP), 4-succinimidyl-oxycarbonyl-α-methyl-α-(2-pyridyldithio)-toluene (SMPT), N-succinimidyl-3-(2-pyridyldithio)butyrate (SDPB), succinimidyl pyridyl-dithio-propionate (SPDP), 4-(2-pyridyldithio)butanoic acid N-hydrosuccinimide ester (SPDB), succinimidyl 4-[N-maleimidomethyl]cyclohexane-1-carboxylate (SMCC), N-sulfosuccinimidyl-3-(2-(5-nitro-pyridyldithio) butyrate (SSNPB), 2-iminothiolate, or S-acetylsuccinic anhydride by known methods. See, Carlsson et al., 173, *Biochem J.* 723-737 (1978); Blattler et al., 24, *Biochem.* 1517-1524 (1985); Lambert et al., 22, *Biochem.* 3913-3920 (1983); Klotz et al., 96, *Arch Biochem. Biophys.*, 605 (1962); and Liu et al., 18, *Biochem.*, 690 (1979); Blakey and Thorpe, 1 *Antibody, Immunoconjugates & Radio-pharmaceuticals*, 1-16 (1988); Worrel et al. 1 Anti-Cancer Drug Design 179-184 (1986). The free or protected thiol-containing cell binding agent thus derived is then reacted with a disulfide- or thiol-containing leptomycin derivative to produce conjugates.

The conjugates made by the above methods can be purified by standard column chromatography or by HPLC.

Preferably conjugates between monoclonal antibodies or cell binding agents and leptomycin derivatives of the present invention are those that are joined via a disulfide bond, or thioether bond as discussed above. Such cell binding conjugates are prepared by known methods such as modifying monoclonal antibodies with succinimidyl pyridyl-dithiopropionate (SPDP) {Carlsson et al, 173 Biochem. J. 723-737 (1978)}. The resulting thiopyridyl group is then displaced by treatment with thiol containing leptomycin derivative to produce disulfide linked conjugates. Conjugates containing 1 to 10 leptomycin derivatives linked via a disulfide bridge are readily prepared by this method. Conjugation by this method is fully described in U.S. Pat. No. 5,585,499, which is incorporated by reference.

In Vitro Cytotoxicity of Conjugates Between Cell Binding Agents and Leptomycin Derivatives of the Present Invention Cytotoxicity of the leptomycin derivatives of the present invention and their conjugates with cell binding agents can be measured after cleavage of the protecting group and conversion into the active drug. Cytotoxicity to non-adherent cell lines such as Namalwa and HL60 can be measured by back-extrapolation of cell proliferation curves as described in Goldmacher et al, 135, J. Immunol. 3648-3651 (1985). Cytotoxicity of these compounds to adherent cell lines such as A-375 and SCaBER can be determined by clonogenic assays as described in Goldmacher et al, 102 J. Cell Biol. 1312-1319 (1986).

Therapeutic Agent and Method for Inhibiting the Growth of Selected Cell Populations The present invention also provides a therapeutic agent for inhibiting the growth of selected cell populations comprising:

(a) a cytotoxic amount of one or more of the above-described leptomycin derivatives linked to a cell binding agent, and (b) a pharmaceutically acceptable carrier, diluent or excipient.

Similarly, the present invention provides a method for inhibiting the growth of selected cell populations comprising contacting a cell population or tissue suspected of containing cells from said selected cell population with a cytotoxic amount of a cytotoxic agent comprising one or more of the above-described leptomycin derivatives linked to a cell binding agent.

The cytotoxic agent is prepared as described above.

Suitable pharmaceutically acceptable carriers, diluents, and excipients are well known and can be determined by those of skill in the art as the clinical situation warrants.

Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

The method for inhibiting the growth of selected cell populations can be practiced in vitro, in vivo, or ex vivo.

Examples of in vitro uses include treatments of cell cultures in order to kill all cells except for desired variants that do not express the target antigen; or to kill variants that express undesired antigen.

The conditions of non-clinical in vitro use are readily determined by the skilled artisan.

Examples of ex vivo uses include treatments of autologous bone marrow prior to their transplant into the same patient in order to kill diseased or malignant cells: treatments of bone marrow prior to their transplantation in order to kill competent T cells and prevent graft-versus-host-disease (GVHD).

Clinical ex vivo treatment to remove tumor cells or lymphoid cells from bone marrow prior to autologous transplantation in cancer treatment or in treatment of autoimmune disease, or to remove T cells and other lymphoid cells from allogeneic bone marrow or tissue prior to transplant in order to prevent GVHD, can be carried out as follows. Bone marrow is harvested from the patient or other individual and then incubated in medium containing serum to which is added the cytotoxic agent of the invention, concentrations range from about 10 µM to 1 pM, for about 30 minutes to about 48 hours at about 37° C. The exact conditions of concentration and time of incubation (=dose) are readily determined by the skilled artisan. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as solutions that are tested for sterility and for endotoxin levels or as a lyophilized solid that can be redissolved in sterile water for injection. Examples of suitable protocols of conjugate administration are as follows. Conjugates are given weekly for 6 weeks as an i.v. bolus. Bolus doses are given in 50 to 400 ml of normal saline to which human serum albumin (e.g. 0.5 to 1 mL of a concentrated solution of human serum albumin, 100 mg/mL) can be added. Dosages will be about 50 µg to 10 mg/kg of body weight per week, i.v. (range of 10 µg to 100 mg/kg per injection). Six weeks after treatment, the patient may receive a second course of treatment. Specific clinical protocols with regard to route of administration, excipients, diluents, dosages, times, etc., can be determined by the skilled artisan as the clinical situation warrants.

Examples of medical conditions that can be treated according to the in vivo or ex vivo methods of killing selected cell populations include malignancy of any type including, for example, cancer of the lung, breast, colon, prostate, kidney, pancreas, ovary, and lymphatic organs; melanomas; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc; bacterial infection; and parasite infections, such as giardiasis, amoebiasis, schistosomiasis, and others as determined by one skilled in the art.

EXAMPLES

The invention will now be illustrated by reference to non-limiting examples. Unless otherwise stated, all percents, ratios, parts, etc. are by weight.

Materials and Methods

Melting points were measured using an Electrothermal apparatus and are uncorrected. NMR spectra were recorded on a Bruker AVANCE400 (400 MHz) spectrometer. Chemical shifts are reported in ppm relative to TMS as an internal standard. Mass spectra were obtained using a Bruker Esquire 3000 system. Ultraviolet spectra were recorded on a Hitachi U1200 spectrophotometer. HPLC was performed using a Beckman Coulter GOLD 125 system equipped with a Beckman Coulter system GOLD 168 variable wavelength detector and a Waters RADIALPAK, (a reverse phase C-18 column). Thin layer chromatography was performed on Analtech GF silica gel TLC plates. Silica gel for flash column chromatography was from Baker. Tetrahydrofuran was dried by distillation over sodium metal. Dimethylactamide and dimethylformamide were dried by distillation over calcium hydride under reduced pressure. All other solvents used were reagent grade or HPLC grade.

The human cancer cell lines HL60, Namalwa, A-375, COLO205 and Ramos were obtained from the American Type Culture Collection (ATCC). Kara is a murine tumor cell line that has been stably transfected with the human CD33 antigen.

Experimental Part

Mass spectrometry analysis was conducted as follows:

EI-CI Analysis: direct introduction (DCI=sample deposit on filament) Mass spectrometer Finnigan SSQ7000; mass range m/z=29-900; electron energy 70 eV; source temperature 70° C.; reactant gas CI ammoniac; EI=Ionisation through electronic impact; CI=Chemical Ionisation.

Electrospray analysis: (positive electrospray: ES$^+$; negative electrospray: ES$^-$)

LC-MS-DAD-ELSD:

MS: Waters-Micromass ZQ; LC: Agilent HP 1100; LC column Xbridge Waters C18, 3×50 mm, 2.5 μm; eluent: gradient water (with 0.1% formic acid)+acetonitrile; UV: DAD (λ=200-400 nm).

Example 1

(2-Methylsulfanyl-ethyl)-amide of (2E,10E,12E,16Z,18E)-(R)-6-Hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic Acid To a solution of 20 mg of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid and 5.6 mg of HOBT (1-hydroxybenzotriazole) in 0.3 ml of dichloromethane, are introduced at a temperature near 20° C., 7.65 μl of DIC (N,N'-diisopropylcarbodiimide) then 5.2 mg of 2-(thiomethyl)ethylamine. The reaction mixture is stirred at a temperature near 20° C. during 20.5 hours, then purified by direct deposit on 2 preparative silica gel TLC plates (thickness 0.5 mm, 20×20 cm). The preparative TLC plates were eluted with a mixture of methanol/dichloromethane (5/95 in volumes) then the desired product is extracted from silica gel with a mixture of methanol/dichloromethane (15/85 in volumes).

1.4 mg of (2-methylsulfanyl-ethyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid are obtained as a yellow solid whose characteristics are the following:

Mass Spectra:

CI: m/z=617: [M+NH$_4$]$^+$; m/z=600: [M+H]$^+$

1H NMR spectra at 600 MHz obtained on a spectrometer BRUKER AVANCE DMX-600 with the following chemical shifts (δ in ppm)—in chloroform as solvent—d1 (CDCl3-d1) reference at 7.27 at a temperature of 303K: 0.79 (d, J=6.5 Hz, 3H); 0.97 (d, J=7.0 Hz, 3H); 1.07 (d, J=7.0 Hz, 3H); 1.12 (d, J=7.0 Hz, 3H); 1.15 (d, J=7.5 Hz, 3H); 1.71 (m, 1H); 1.81 (s, 3H); 1.82 (m partially masked, 1H); 1.83 (s, 3H); 2.08 (m, 2H); 2.11 (s, 3H); 2.13 (s, 3H); 2.15 (dd, J=6.5 and 13.5 Hz, 1H); 2.45 (m broad, 1H); 2.53 (m, 1H); 2.66 (t, J=6.5 Hz, 2H); 2.70 (m, 1H); 2.82 (m, 1H); 3.50 (q, J=6.5 Hz, 2H); 3.61 (m, 1H); 3.65 (m, 1H); 5.01 (dd, J=4.5 and 7.5 Hz, 1H); 5.09 (d, J=10.0 Hz, 1H); 5.26 (d, J=10.0 Hz, 1H); from 5.55 to 5.66 (m, 2H); 5.69 (dd, J=7.5 and 16.0 Hz, 1H); 5.97 (t broad,

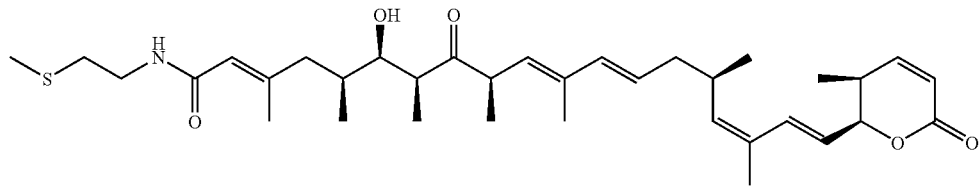

J=6.5 Hz, 1H); 6.00 (d, J=10.0 Hz, 1H); 6.02 (d, J=15.5 Hz, 1H); 6.75 (d, J=16.0 Hz, 1H); 6.95 (dd, J=6.0 and 10.0 Hz, 1H).

Example 2

Bis-[(2-mercaptoethyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic Acid]

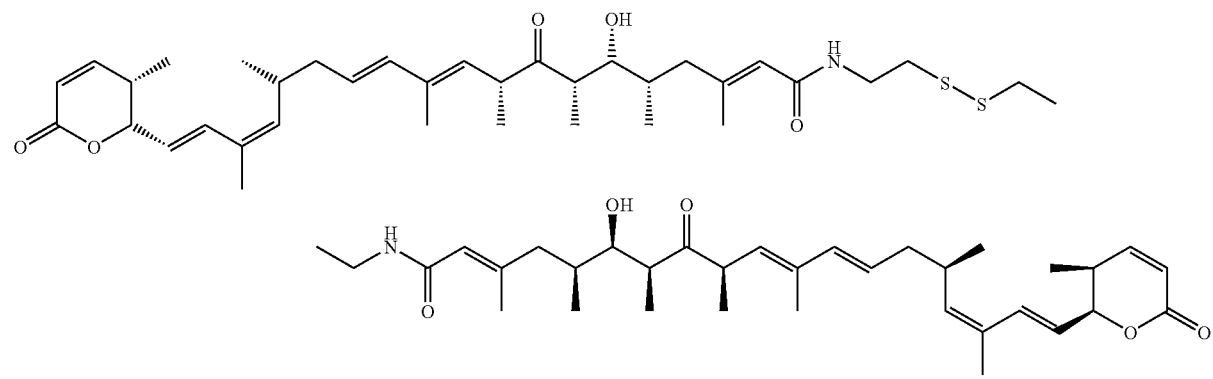

To a solution of 20 mg of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid and 5.6 mg of HOBT (1-hydroxybenzotriazole) in 0.3 ml of dichloromethane, are introduced at a temperature near 20° C., 12.8 mg of dichlorhydrate of cystamine, 7.65 μl of DIC(N,N'-diisopropylcarbodiimide) then 11.6 μl of triethylamine. The reaction mixture is stirred at a temperature near 20° C. during 22 hours, then purified by direct deposit on 2 preparative silica gel TLC plates (thickness 0.5 mm, 20×20 cm). The preparative TLC plates were eluted with a mixture of methanol/dichloromethane (5/95 in volumes) then the desired product is extracted from silica gel with a mixture of methanol/dichloromethane (15/85 in volumes). 4.6 mg of bis-[(2-thioethyl)-amide of (2E,10E,12E,16Z,18E)-(R)-6-hydroxy-3,5,7,9,11,15,17-hepta-methyl-19-((2S,3S)-3-methyl-6-oxo-3,6-dihydro-2H-pyran-2-yl)-8-oxo-nonadeca-2,10,12,16,18-pentaenoic acid] are obtained as a white solid whose characteristics are the following:

Mass Spectra:
ES$^+$: m/z=1167: [M+H]$^+$
ES$^-$: m/z=1211: [M−H+ HCOOH]$^-$

Example 3

(2-Mercapto-ethyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic Acid dichloromethane (8/92 in volumes) then the desired product is extracted from silica gel with a mixture of methanol/dichloromethane (15/85 in volumes). 2.3 mg of (2-Mercapto-ethyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid are obtained as a colorless glass whose characteristics are the following:

Mass Spectra:
ES$^+$: m/z=586: [M+H]$^+$
ES$^-$: m/z=630: [M−H+HCOOH]$^-$

1H NMR spectra at 400 MHz obtained on a spectrometer BRUKER AVANCE DRX-400 with the following chemical shifts (δ in ppm)—in chloroform as solvent—d1 (CDCl$_3$-d1) reference at 7.27 at a temperature of 303K: 0.80 (d, J=6.5 Hz, 3H); 0.98 (d, J=6.5 Hz, 3H); 1.08 (d, J=7.5 Hz, 3H); 1.14 (d, J=6.5 Hz, 3H); 1.16 (d, J=7.0 Hz, 3H); 1.72 (m, 1H); from 1.80 to 1.87 (m masked, 1H); 1.82 (s, 3H); 1.84 (s, 3H); 2.09 (m, 2H); 2.11 (s, 3H); 2.16 (dd, J=6.5 and 13.5 Hz, 1H); 2.54 (m, 1H); from 2.65 to 2.74 (m, 3H); 2.83 (m, 1H); 3.48 (q, J=6.5 Hz, 2H); from 3.60 to 3.70 (m, 2H); 5.00 (dd, J=4.0 and 7.0 Hz, 1H); 5.10 (d, J=10.5 Hz, 1H); 5.27 (d, J=10.5 Hz, 1H); 5.58 (s, 1H); 5.60 (td partially masked, J=7.5 and 15.5 Hz, 1H); 5.70 (dd, J=7.0 and 15.5 Hz, 1H); from 5.96 to 6.06 (m, 3H); 6.75 (d broad, J=15.5 Hz, 1H); 6.97 (dd, J=6.0 and 10.0 Hz, 1H).

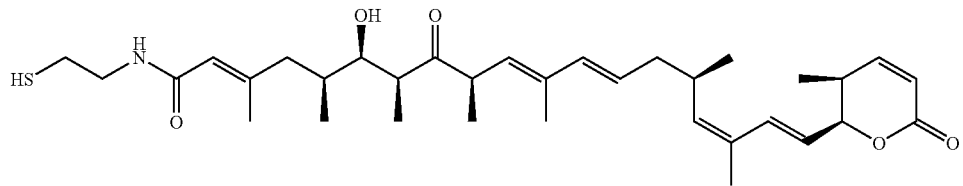

To a solution of 20 mg of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid and 8 μl of triethylamine in 0.15 ml of dichloromethane, is introduced at a temperature near 0° C., 6.1 μl of pivaloyl chloride. After 15 minutes at a temperature near 0° C., a solution of 4.4 mg of 2-aminoethanethiol in 0.15 ml of dichloromethane and 0.05 ml of ethanol is added.

Example 4

(2-Methyldisulfanyl-ethyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic Acid

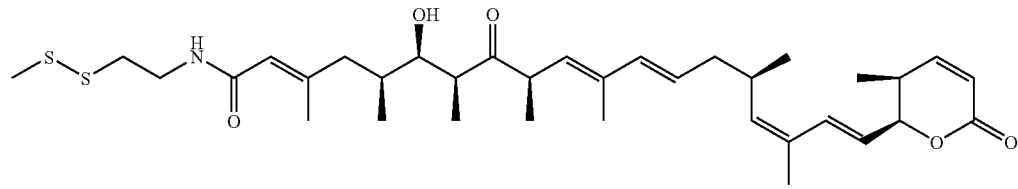

The reaction mixture is stirred at a temperature near 20° C. for 1 hour, then purified by direct deposit on 2 preparative silica gel TLC plates (thickness 0.5 mm, 20×20 cm). The preparative TLC plates were eluted with a mixture of methanol/

To a solution of 20 mg of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid and 5.6 mg of HOBT (1-hydroxybenzotriazole) in 0.15 ml of dichloromethane, are introduced at a temperature near 20° C., 7.65 μl of DIC (N,N'-diisopropylcarbodiimide) then a solution of 8 mg of 2-methyldithio-ethylamine in 0.15 ml of dichloromethane. The reaction mixture is stirred at a temperature near 20° C. during 2 hours, then purified by direct deposit on 2 preparative silica gel TLC plates (thickness 0.5 mm, 20×20 cm). The preparative TLC plates were eluted with a mixture of methanol/dichloromethane (7/93 in volumes) then the desired product is extracted from silica gel with a mixture of methanol/dichloromethane (15/85 in volumes). 3.4 mg (2-methyldisulfanyl-ethyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid are obtained as a pale yellow oil whose characteristics are the following:

Mass Spectra:
ES$^+$: m/z=632: [M+H]$^+$
ES$^-$: m/z=630: [M−H]$^-$; m/z=676: [M−H+ HCOOH]$^-$
1H NMR spectra at 400 MHz obtained on a spectrometer BRUKER AVANCE DRX-400 with the following chemical shifts (δ in ppm)—in chloroform as solvent—d1 (CDCl$_3$-d1) reference at 7.27 at a temperature of 303K: 0.81 (d, J=6.5 Hz, 3H); 0.98 (d, J=6.5 Hz, 3H); 1.08 (d, J=7.5 Hz, 3H); 1.14 (d, J=6.5 Hz, 3H); 1.16 (d, J=7.0 Hz, 3H); 1.72 (m, 1H); from 1.79 to 1.86 (m, 1H); 1.82 (s, 3H); 1.84 (s, 3H); 2.09 (m, 2H); 2.11 (s broad, 3H); 2.15 (dd, J=5.5 and 13.5 Hz, 1H); 2.35 (s broad, 1H); 2.43 (m, 3H); 2.54 (m, 1H); 2.70 (m, 1H); 2.83 (m, 1H); 2.86 (t, J=6.5 Hz, 2H); from 3.59 to 3.70 (m, 4H); 5.01 (dd, J=4.0 and 7.0 Hz, 1H); 5.11 (d, J=10.0 Hz, 1H); 5.27 (d, J=10.0 Hz, 1H); 5.56 (s, 1H); 5.60 (td partially masked, J=7.5 and 15.5 Hz, 1H); 5.70 (dd, J=7.0 and 15.5 Hz, 1H); 5.93 (t, J=6.0 Hz, 1H); 6.00 (d, J=10.0 Hz, 1H); 6.02 (d, J=15.5 Hz, 1H); 6.75 (d, J=15.5 Hz, 1H); 6.96 (dd, J=6.0 and 10.0 Hz, 1H).

Example 5

(2-Methyl-2-methyldisulfanyl-propyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic Acid To a solution of 225.4 mg of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid in 1.5 ml of dichloromethane are introduced, at a temperature near 0° C., a solution of 63.6 mg of HOBT (1-hydroxybenzotriazole) and 110 mg of 2-methyl-2-methyldisulfanyl-propylamine in 1.5 ml of dichloromethane, then 86.2 μl of DIC(N,N'-diisopropylcarbodiimide). The reaction mixture is stirred at a temperature near 0° C. for 15 hours, then is diluted with 30 ml of dichloromethane. The organic phase is washed twice with 10 ml of water, dried on sodium sulfate, filtrated on sintered glass, then concentrated under reduced pressure at a temperature near 40° C. The so-obtained residue is purified by column chromatography on silica gel (20 g SiO$_2$ 15-35 μm, elution gradient methanol/dichloromethane from 0/100 to 10/90 (in volumes). Fractions containing the desired product are concentrated under reduced pressure at a temperature near 40° C. 212.1 mg of (2-methyl-2-methyldisulfanyl-propyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid are obtained as a yellow glass whose characteristics are the following:

Mass Spectra:
ES$^+$: m/z=660: [M+H]$^+$
ES$^-$: m/z=658: [M−H]$^-$; m/z=704: [M−H+HCOOH]$^-$
1H NMR spectra at 400 MHz obtained on a spectrometer BRUKER AVANCE DRX-400 with the following chemical shifts (δ in ppm)—in chloroform as solvent—d1 (CDCl$_3$-d1) reference at 7.27 at a temperature of 303K: 0.80 (d, J=6.5 Hz, 3H); 0.97 (d, J=6.5 Hz, 3H); 1.08 (d, J=7.5 Hz, 3H); 1.14 (d, J=6.5 Hz, 3H); 1.16 (d, J=7.0 Hz, 3H); 1.32 (s, 6H); 1.72 (m, 1H); 1.82 (s, 3H); 1.83 (m masked, 1H); 1.84 (s, 3H); 2.08 (m, 2H); 2.11 (s broad, 3H); 2.15 (dd, J=6.5 and 13.5 Hz, 1H); 2.43 (s, 3H); 2.54 (m, 1H); 2.70 (m, 1H); 2.83 (m, 1H); 3.45 (d, J=6.0 Hz, 2H); from 3.59 to 3.69 (m, 2H); 5.00 (dd, J=4.0 and 7.0 Hz, 1H); 5.10 (d, J=10.5 Hz, 1H); 5.26 (d, J=10.0 Hz, 1H); from 5.54 to 5.64 (m, 2H); 5.70 (dd, J=7.0 and 15.5 Hz, 1H); 5.83 (t, J=6.0 Hz, 1H); 6.00 (d, J=10.5 Hz, 1H); 6.02 (d, J=15.5 Hz, 1H); 6.75 (d, J=15.5 Hz, 1H); 6.96 (dd, J=6.5 and 10.5 Hz, 1H).

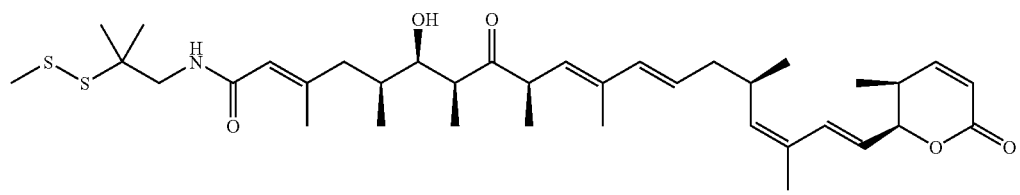

Example 6

(2-Mercapto-2-methyl-propyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic Acid

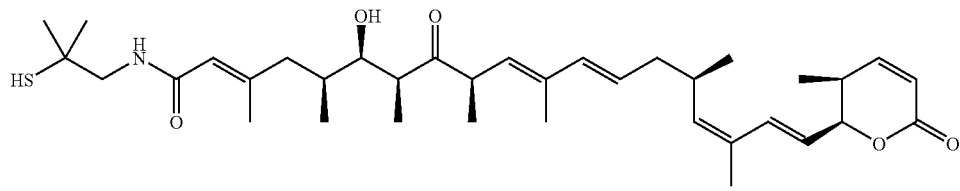

To a solution of 200 mg of (2-methyl-2-methyldisulfanyl-propyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid in 7.7 ml of tetrahydrofurane and 3.85 ml of water, at a temperature near 20° C., is added 217.2 mg of TCEP (chlorhydrate of tris(2-carboxyethyl)phosphine). After 16 hours at a temperature near 20° C., the reaction mixture is diluted with 30 ml of ethyl acetate, washed twice with 15 ml of water, 15 ml of brine, dried on magnesium sulfate, filtered on sintered glass and concentrated under reduced pressure at a temperature near 40° C. The so-obtained yellow oil is purified by column chromatography on silica gel (25 g $SiO_2$ 15-35 µm, elution gradient methanol/dichloromethane from 1/99 to 10/90 (in volumes)). Fractions containing the desired product are concentrated under reduced pressure at a temperature near 40° C. 122.6 mg of (2-mercapto-2-methyl-propyl)-amide of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid are obtained as a yellow glass whose characteristics are the following:

Mass Spectra:
ES$^+$: m/z=614: [M+H]$^+$
ES$^-$: m/z=612: [M−H]$^-$; m/z=658: [M−H+HCOOH]$^-$ 1H NMR spectra at 500 MHz obtained on a spectrometer BRUKER AVANCE DRX-500 with the following chemical shifts (δ in ppm)—in chloroform as solvent—d1 ($CDCl_3$-d1) reference at 7.27 at a temperature of 303K: 0.80 (d, J=6.5 Hz, 3H); 0.97 (d, J=6.5 Hz, 3H); 1.07 (d, J=7.5 Hz, 3H); 1.13 (d, J=6.5 Hz, 3H); 1.16 (d, J=6.5 Hz, 3H); 1.38 (s, 6H); 1.72 (m, 1H); 1.82 (s, 3H); 1.84 (s, 3H); 1.85 (m partially masked, 1H); 2.09 (m, 2H); 2.11 (s, 3H); 2.17 (dd, J=6.5 and 13.5 Hz, 1H); 2.54 (m, 1H); 2.70 (m, 1H); 2.83 (m, 1H); 3.38 (d, J=6.5 Hz, 2H); from 3.61 to 3.70 (m, 2H); 5.01 (dd, J=4.0 and 7.0 Hz, 1H); 5.09 (d, J=10.0 Hz, 1H); 5.26 (d, J=10.0 Hz, 1H); 5.59 (dt partially masked, J=7.5 and 15.5 Hz, 1H); 5.63 (s, 1H); 5.69 (dd, J=7.0 and 15.5 Hz, 1H); 6.00 (d, J=10.0 Hz, 1H); 6.02 (d, J=15.5 Hz, 1H); 6.04 (t partially masked, J=6.5 Hz, 1H); 6.75 (d, J=15.5 Hz, 1H); 6.97 (dd, J=6.0 and 10.0 Hz, 1H).

Conjugation of Antibodies with Leptomycin Derivatives:
Conjugation of Anti-Colon Cancer Antibody huC242 with Leptomycin Derivatives:

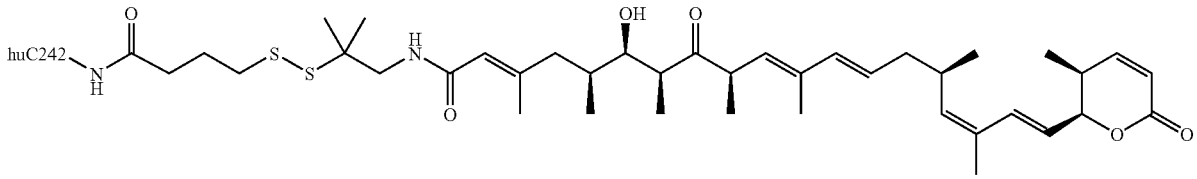

A disulfide-linked conjugate of a humanized anti-colon tumor antibody (huC242) with the compound of example 6 was prepared (herein referred to as huC242-SSNPB-leptomycin of example 6). The huC242 antibody was reacted with a 6-fold molar excess of the antibody modifying agent SSNPB (N-sulfosuccinimidyl 4-(5-nitro-2-pyridyldithio)butanoate) at an antibody concentration of 9 mg/ml in 50 mM potassium phosphate buffer (pH 6.5, containing 50 mM NaCl, 2 mM EDTA, 5% dimethylacetamide) for 90 minutes at ambient temperature. The reaction mixture was purified by Sephadex G-25 size-exclusion chromatography equilibrated in 50 mM potassium phosphate buffer pH 6.5, containing 50 mM NaCl and 2 mM EDTA. The modified antibody sample was assayed with and without addition of β-mercaptoethanol and determined to have ~6 nitropyridyldithio groups incorporated per antibody. A 2-fold molar excess of Leptomycin-SH drug per linker group was added to the modified antibody sample at 2 mg/ml in 50 mM potassium phosphate buffer (pH 6.5, containing 50 mM NaCl, 2 mM EDTA, 10% dimethylacetamide). The reaction was followed spectrophotometrically (394 nm) and by HPLC for the release of 5-nitropyridine-2-thione. After reaction at ambient temperature for about 90 min, the mixture was purified by Sephadex G-25 size-exclusion chromatography in 50 mM potassium phosphate buffer (pH 6.5, containing 50 mM NaCl, 2 mM EDTA). The absorbance ratio at 250 nm/280 nm of 0.78 for the conjugate versus 0.37 for the unmodified antibody demonstrated the incorporation of leptomycin group in the conjugate (resulting in increased absorbance at 250 nm).

Mass spectrometric analysis of a deglycosylated huC242-leptomycin conjugate showed conjugate peaks at 147492, 148212, 148936, and 149660 dalton corresponding to 1, 2, 3, and 4 leptomycin molecules incorporated per antibody molecule.

Conjugation of Anti-CD19 (huB4) Antibody with Leptomycin Derivatives:

Conjugates of anti-CD19 antibody (humanized B4 antibody) with leptomycin were prepared with disulfide and non-cleavable thioether linkers. The first sample (—S—S— linker) consisted of anti-CD19 (huB4) antibody linked to the compound of example 6 via the disulfide linker SSNPB (N-sulfosuccinimidyl 4-(5-nitro-2-pyridyl-dithio)butanoate). The second sample consisted of huB4 antibody linked to the compound of example 6 via the maleimide linker SMCC(N-succinimidyl 4-(maleimido-methyl)cyclohexanecarboxylate).

HuB4-SSNPB-Leptomycin Conjugate (huB4-SSNPB-Leptomycin of Example 6):

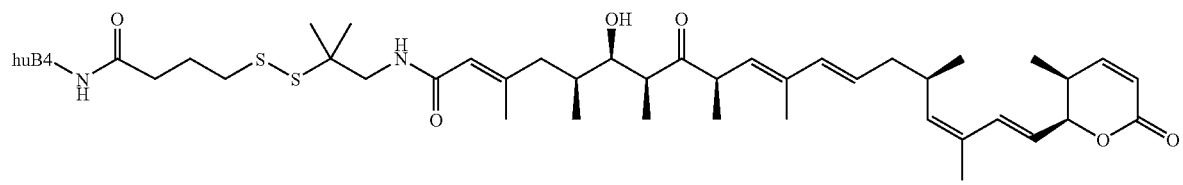

4 mg of huB4 antibody was reacted with a 7.5-fold molar excess of SSNPB linker at an antibody concentration of 8 mg/ml in 50 mM potassium phosphate buffer (pH 6.5, containing 50 mM NaCl, 2 mM EDTA, 5% dimethylacetamide) for 90 minutes at ambient temperature. The reaction mixture was purified by Sephadex G-25 size-exclusion chromatography in 50 mM potassium phosphate buffer (pH 6.5, containing 50 mM NaCl, 2 mM EDTA). The modified antibody sample was assayed with and without addition of β-mercaptoethanol and determined to have 5.3 nitropyridyldithio groups incorporated per antibody. A 3-fold molar excess of the drug of example 6 per linker group was added to the modified antibody sample at 1 mg/ml in 50 mM potassium phosphate buffer (pH 6.5, containing 50 mM NaCl, 2 mM EDTA, 10% dimethylacetamide). The reaction was followed spectrophotometrically (394 nm) and by HPLC for the release of 5-nitropyridine-2-thione. After overnight reaction at ambient temperature the mixture was purified by Sephadex G-25 size-exclusion chromatography in 10 mM citrate buffer (pH 5.5, containing 135 mM NaCl). The sample was assayed with and without addition of β-mercaptoethanol and determined to have 4.3 reacted linkers per antibody. Size-exclusion chromatography (SEC) analysis showed 95% monomeric antibody.

HuB4-SMCC-Leptomycin Conjugate:

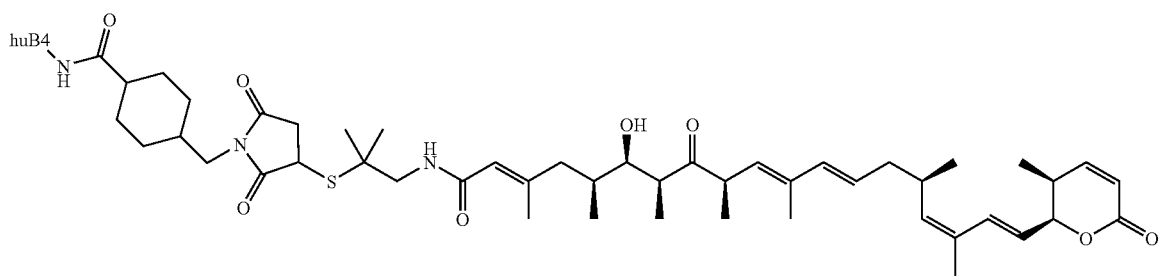

4 mg of huB4 antibody was reacted with a 7.5-fold molar excess of SMCC linker at an antibody concentration of 8 mg/ml in 50 mM potassium phosphate buffer (pH 6.5, containing 50 mM NaCl, 2 mM EDTA, 5% dimethylacetamide) for 90 minutes at ambient temperature. The reaction mixture was purified by Sephadex G-25 size-exclusion chromatography in 50 mM potassium phosphate buffer (pH 6.5, containing 50 mM NaCl, 2 mM EDTA). The number of maleimide groups incorporated in the sample was assayed by adding an excess of a thiol (cysteine) and determined to have 3.3 linker groups per antibody. A 3-fold molar excess of the drug of example 6 per maleimide group was added to the modified antibody sample at 1 mg/ml in 50 mM potassium phosphate buffer (pH 6.5, containing 50 mM NaCl, 2 mM EDTA, 10% dimethylacetamide). After overnight reaction at ambient temperature the mixture was purified by Sephadex G-25 size-exclusion chromatography in 10 mM citrate buffer (pH 5.5, containing 135 mM NaCl). SEC analysis showed 98% monomeric antibody.

Mass spectrometric analysis of a deglycosylated huB4-SSNPB-leptomycin conjugate showed conjugate peaks at 145138, 145860 and 146566 dalton corresponding to 1, 2, and 3 leptomycin molecules incorporated per antibody molecule.

Biological Results:

Cytotoxicity evaluation of a huB4-SSNPB-leptomycin of example 6 conjugate on Ramos (CD19 antigen-positive) and HL60 (antigen negative) cancer cells by WST-viability assay showed $IC_{50}$ values of $1.4 \times 10^{-9}$ M and $4.2 \times 10^{-9}$ M, respectively, thus demonstrating the antigen-specific cytotoxic activity of the leptomycin-antibody conjugate.

Cytotoxicity evaluation of the huC242-SSNPB-leptomycin of example 6 conjugate on COLO 205 (CanAg antigen-positive) cancer cells and A375 cells showed $IC_{50}$ value of $1.3 \times 10^{-10}$ M and $>5.0 \times 10^{-9}$ M, respectively. (FIG. 1).

Certain patents and printed publications have been referred to in the present disclosure, the teachings of which are hereby each incorporated in their respective entireties by reference.

While the invention has been described in detail and with reference to specific embodiments thereof, it will be apparent to one of skill in the art that various changes and modifications can be made thereto without departing from the spirit and scope thereof.

What is claimed is:

1. A leptomycin derivative of formula (I):

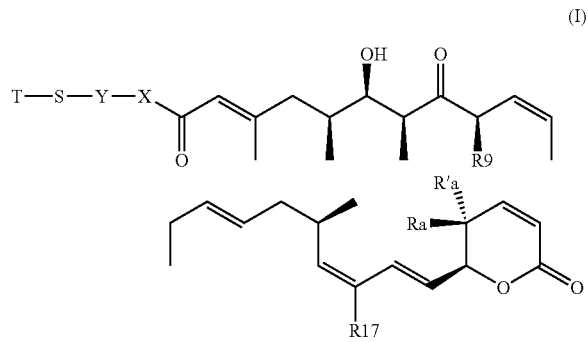

(I)

wherein:
Ra and R'a are independently H or methyl;
R17 is methyl or ethyl;
R9 is methyl optionally substituted by OR, CN, or NRR';
X is —NR—;
Y is a linear or branched $C_1$-$C_{20}$ alkyl;
T represents H or a thiol protecting group or T represents

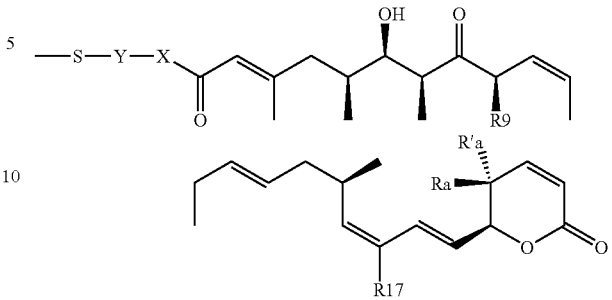

where:
Ra, R'a, R17, R9, X, and Y are defined as above; and
R and R', which may be identical or different, are H or a linear or branched $C_1$-$C_{20}$ alkyl; or a pharmaceutically acceptable salt thereof.

2. The leptomycin derivative according to claim 1 wherein the thiol protecting group is Ac, $R_1$ or $SR_1$, where $R_1$ is H, methyl or a linear or branched $C_1$-$C_{20}$ alkyl, or a pharmaceutically acceptable salt thereof.

3. The leptomycin derivative according to claim 1 wherein Ra is methyl and R'a is H, or a pharmaceutically acceptable salt thereof.

4. The leptomycin derivative according to claim 2 wherein Ra is methyl and R'a is H, or a pharmaceutically acceptable salt thereof.

5. The leptomycin derivative according to claim 1 wherein R9 is methyl, or a pharmaceutically acceptable salt thereof.

6. The leptomycin derivative according to claim 2 wherein R9 is methyl, or a pharmaceutically acceptable salt thereof.

7. The leptomycin derivative according to claim 1 wherein T is H or $SR_1$ where $R_1$ is a linear or branched $C_1$-$C_{20}$ alkyl, or a pharmaceutically acceptable salt thereof.

8. The leptomycin derivative according to claim 1 wherein:
Ra is methyl;
R'a is H;
R9 is methyl; and
T is H or $SR_1$ where $R_1$ is a linear or branched $C_1$-$C_{20}$ alkyl; or a pharmaceutically acceptable salt thereof.

9. A leptomycin derivative which is
(2-Methylsulfanyl-ethyl)-amide of (2E,10E,12E,16Z, 18E)-(R)-6-Hydroxy-3,5, 7,9,11,15,17-heptamethyl-19-((2S,3S)-3-methyl-6-oxo-3,6-dihydro-2H-pyran-2-yl)-8-oxo-nonadeca -2,10,12,16,18-pentaenoic acid;
Bis-[(2-mercaptoethyl)-amide of (2E,10E,12E,16Z,18E)-(R)-6-hydroxy-3,5,7,9,11,15,17-heptamethyl-19-((2S, 3S)-3-methyl-6-oxo-3,6-dihydro-2H-pyran-2-yl)-8-oxo-nonadeca -2,10,12,16,18-pentaenoic acid];
(2-Mercapto-ethyl)-amide of (2E,10E,12E,16Z,18E)-(R)-6-hydroxy-3,5,7,9,11, 15,17-heptamethyl-19-((2S,3S)-3-methyl-6-oxo-3,6-dihydro-2H-pyran-2-yl)-8-oxo-nonadeca-2,10,12,16,18-pentaenoic acid;
(2-Methyldisulfanyl-ethyl)-amide of (2E,10E,12E,16Z, 18E)-(R)-6-hydroxy -3,5,7,9,11,15,17-heptamethy1-19-((2S,3S)-3-methyl-6-oxo-3,6-dihydro-2H-pyran-2-yl)-8-oxo-nonadeca-2,10,12,16,18-pentaenoic acid;
(2-Methyl-2-methyldisulfanyl-propyl)-amide of (2E,10E, 12E,16Z,18E)-(R)-6-hydroxy -3,5,7,9,11,15,17-heptamethyl-19-((2S,3S)-3-methyl-6-oxo-3,6-dihydro-2H-pyran-2-yl)-8-oxo-nonadeca -2,10,12,16,18-pentaenoic acid; or.

(2-Mercapto-2-methyl-propyl)-amide of (2E,10E,12E, 16Z,18E)-(R)-6-hydroxy -3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid; or or a pharmaceutically acceptable salt thereof.

10. A pharmaceutical composition comprising the leptomycin derivative according to claim 1, or a pharmaceutically acceptable salt thereof and a pharmaceutically acceptable carrier.

11. A pharmaceutical composition comprising the leptomycin derivative according to claim 2, or a pharmaceutically acceptable salt thereof, and a pharmaceutically acceptable carrier.

12. A pharmaceutical composition comprising the leptomycin derivative according to claim 9, or a pharmaceutically acceptable salt thereof, and a pharmaceutically acceptable carrier.

13. A conjugate which is prepared by a process comprising the step of reacting the leptomycin derivative according to claim 1 with a modified cell binding agent comprising a function reactive towards the linking group of the leptomycin derivative, so that the derivative and the cell binding agent are linked together via said linker comprising said linking group.

14. The conjugate according to claim 13, wherein said modified cell binding agent comprising a function reactive towards said linking group of the derivative is obtained by reacting said cell binding agent with a reagent chosen from SMCC, SSNPB, LC-SMCC, SIAB, SIA, SBA and SPAP.

15. The conjugate according to claim 13, wherein the leptomycin derivative is
(2-Methylsulfanyl-ethyl)-amide of (2E,10E,12E,16Z, 18E)-(R)-6-Hydroxy-3,5,7,9,11,15,17-heptamethyl-19-((2S,3S)-3-methyl-6-oxo-3,6-dihydro-2H-pyran-2-yl)-8-oxo-nonadeca -2,10,12,16,18-pentaenoic acid;
Bis-[(2-mercaptoethyl)-amide of (2E,10E,12E,16Z,18E)-(R)-6-hydroxy-3,5,7,9, 11,15,17-heptamethyl-19-((2S, 3S)-3-methyl-6-oxo-3,6-dihydro-2H-pyran-2-yl)-8-oxo-nonadeca -2,10,12,16,18-pentaenoic acid];
(2-Mercapto-ethyl)-amide of (2E,10E,12E,16Z,18E)-(R)-6-hydroxy-3,5,7,9,11, 15,17-heptamethyl-19-((2S,3S)-3-methyl-6-oxo-3,6-dihydro-2H-pyran-2-yl)-8-oxo-nonadeca -2,10,12,16,18-pentaenoic acid;
(2-Methyldisulfanyl-ethyl)-amide of (2E,10E,12E,16Z, 18E)-(R)-6-hydroxy -3,5,7,9,11,15,17-heptamethyl-19-((2S,3S)-3-methyl-6-oxo-3,6-dihydro-2H-pyran-2-yl)-8-oxo -nonadeca-2,10,12,16,18-pentaenoic acid;

(2-Methyl-2-methyldisulfanyl-propyl)-amide of (2E,10E, 12E,16Z,18E)-(R)-6-hydroxy -3,5,7,9,11,15,17-heptamethyl-19-((2S,3S)-3-methyl-6-oxo- 3,6-dihydro-2H-pyran-2-yl)-8-oxo -nonadeca-2,10,12,16,18-pentaenoic acid; or.
(2-Mercapto-2-methyl-propyl)-amide of (2E,10E,12E, 16Z,18E)-(R)-6-hydroxy -3,5,7,9,11,15,17-heptamethyl-19-((2S,3S)-3-methyl-6-oxo-3,6-dihydro-2H-pyran-2-yl)-8-oxo -nonadeca-2,10,12,16,18-pentaenoic acid.

16. A conjugate which is prepared by a process comprising the step of reacting the leptomycin derivative according to claim 1 with a cell binding agent comprising a function reactive towards the linking group of the leptomycin derivative, so that the derivative and the cell binding agent are linked together via said linker comprising said linking group.

17. The conjugate according to claim 16, wherein the leptomycin derivative is
(2-Methylsulfanyl-ethyl)-amide of (2E,10E,12E,16Z, 18E)-(R)-6-Hydroxy-3,5, 7,9,11,15,17-heptamethyl-19-((2S,3S)-3-methyl-6-oxo-3 ,6-dihydro-2H-pyran-2-yl)-8-oxo -nonadeca-2,10,12,16,18-pentaenoic acid;
Bis-[(2-mercaptoethyl)-amide of (2E,10E,12E,16Z,18E)-(R)-6-hydroxy-3,5,7,9, 11,15,17-heptamethyl-19-((2S, 3S)-3-methyl-6-oxo-3,6-dihydro-2H-pyran-2-yl)-8-oxo-nonadeca -2,10,12,16,18-pentaenoic acid];
(2-Mercapto-ethyl)-amide of (2E,10E,12E,16Z,18E)-(R)-6-hydroxy-3,5,7,9,11, 15,17-heptamethyl-19-((2S,3S)-3-methyl-6-oxo-3,6-dihydro-2H-pyran-2-yl)-8-oxo-nonadeca -2,10,12,16,18-pentaenoic acid;
(2-Methyldisulfanyl-ethyl)-amide of (2E,10E,12E,16Z, 18E)-(R)-6-hydroxy -3,5,7,9,11,15,17-heptamethyl-19-((2S,3S)-3-methyl-6-oxo-3,6-dihydro-2H-pyran-2-yl)-8-oxo -nonadeca-2,10,12,16,18-pentaenoic acid;
(2-Methyl-2-methyldisulfanyl-propyl)-amide of (2E,10E, 12E,16Z,18E)-(R)-6-hydroxy -3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid; or.
(2-Mercapto-2-methyl-propyl)-amide of (2E,10E,12E, 16Z,18E)-(R)-6-hydroxy -3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid.

* * * * *

UNITED STATES PATENT AND TRADEMARK OFFICE
CERTIFICATE OF CORRECTION

| | | |
|---|---|---|
| PATENT NO. | : 7,816,543 B2 | Page 1 of 2 |
| APPLICATION NO. | : 12/276568 | |
| DATED | : October 19, 2010 | |
| INVENTOR(S) | : Herve Bouchard et al. | |

It is certified that error appears in the above-identified patent and that said Letters Patent is hereby corrected as shown below:

On Title page 2, Item (56), under "Other Publications", line 15, delete "Silycarbocyclization" and insert -- Silylcarbocyclization --, therefor.

On Title page 2, Item (56), under "Other Publications", line 24, delete "Silyformylation" and insert -- Silylformylation --, therefor.

In column 1, line 41, delete "1. Ojima" and insert -- I. Ojima --, therefor.

In column 2, line 31, delete "Steptomyces" and insert -- Streptomyces --, therefor.

In column 6, line 48, delete "pyrrollyl," and insert -- pyrrolyl, --, therefor.

In column 12, line 48, delete "N-hydrosuccinimide" and insert -- N-hydroxysuccinimide --, therefor.

In column 14, line 59, delete "Dimethylactamide" and insert -- Dimethylacetamide --, therefor.

In column 21, line 24, delete "tetrahydrofurane" and insert -- tetrahydrofuran --, therefor.

In column 26, line 60, in claim 9, delete "heptamethy1" and insert -- heptamethyl --, therefor.

In column 26, line 67, in claim 9, delete "acid; or." insert -- acid; or --, therefor.

In column 27, line 2-3, in claim 9, delete "heptamethy1" and insert -- heptamethyl --, therefor.

In column 27, line 5, in claim 9, delete "acid; or or" and insert -- acid; or --, therefor.

In column 27, line 8, in claim 10, delete "thereof" and insert -- thereof, --, therefor.

In column 27, line 44, in claim 15, delete "heptamethy1" and insert -- heptamethyl --, therefor.

Signed and Sealed this
Tenth Day of January, 2012

David J. Kappos
*Director of the United States Patent and Trademark Office*

CERTIFICATE OF CORRECTION (continued)
U.S. Pat. No. 7,816,543 B2

In column 28, line 5, in claim 15, delete "acid; or." and insert -- acid; or --, therefor.

In column 28, line 7-8, in claim 15, delete "heptamethy1" and insert -- heptamethyl --, therefor.

In column 28, line 32, in claim 17, delete "heptamethy1" and insert -- heptamethyl --, therefor.

In column 28, line 39, in claim 17, delete "acid; or." and insert -- acid; or --, therefor.

In column 28, line 41-42, in claim 17, delete "heptamethy1" and insert -- heptamethyl --, therefor.